US008382650B2

(12) United States Patent
Benson

(10) Patent No.: US 8,382,650 B2
(45) Date of Patent: Feb. 26, 2013

(54) CATHETER MARKING FOR MULTI-LUMEN CATHETER IDENTIFICATION

(75) Inventor: Maria Benson, West Boylston, MA (US)

(73) Assignee: Cytyc Corporation, Marlborough, MA (US)

( * ) Notice: Subject to any disclaimer, the term of this patent is extended or adjusted under 35 U.S.C. 154(b) by 676 days.

(21) Appl. No.: 12/463,466

(22) Filed: May 11, 2009

(65) Prior Publication Data

US 2010/0286466 A1 Nov. 11, 2010

(51) Int. Cl.
*A61N 5/00* (2006.01)
(52) U.S. Cl. .......................................................... 600/3
(58) Field of Classification Search .................... 600/1–8
See application file for complete search history.

(56) References Cited

U.S. PATENT DOCUMENTS

| | | |
|---|---|---|
| 3,324,847 A | 6/1967 | Zoumboulis |
| 3,872,856 A | 3/1975 | Clayton |
| 4,350,169 A | 9/1982 | Dutcher et al. |
| 4,417,576 A | 11/1983 | Baran |
| 4,706,652 A | 11/1987 | Horowitz |
| 4,754,745 A | 7/1988 | Horowitz |
| 4,763,642 A | 8/1988 | Horowitz |
| 4,821,725 A | 4/1989 | Azam et al. |
| 4,867,741 A | 9/1989 | Portnoy |
| 5,015,247 A | 5/1991 | Michaelson |
| 5,084,001 A | 1/1992 | Van't Hooft et al. |
| 5,084,015 A | 1/1992 | Moriuchi |
| 5,106,360 A | 4/1992 | Ishiwara et al. |
| 5,112,303 A | 5/1992 | Pudenz et al. |
| 5,152,747 A | 10/1992 | Olivier |
| 5,236,410 A | 8/1993 | Granov et al. |
| 5,422,926 A | 6/1995 | Smith et al. |
| 5,484,384 A | 1/1996 | Fearnot |
| 5,520,646 A | 5/1996 | D'Andrea |
| 5,562,594 A | 10/1996 | Weeks |
| 5,566,221 A | 10/1996 | Smith et al. |
| 5,653,683 A | 8/1997 | D'Andrea |
| 5,720,717 A | 2/1998 | D'Andrea |

(Continued)

FOREIGN PATENT DOCUMENTS

| | | |
|---|---|---|
| DE | 25 39 553 | 3/1977 |
| EP | 0 340 881 | 10/1992 |

(Continued)

OTHER PUBLICATIONS

Ashpole, et al., "A New Technique of Brachytherapy for Malignant Gliomas with Caesium-137: A New Method Utilizing a Remote Afterloading System," Clinical Oncology, p. 333-7, 1990.

(Continued)

*Primary Examiner* — John Lacyk

(57) ABSTRACT

Systems and methods that facilitate visualization and identification of lumens of a multi-lumen brachytherapy device are disclosed. In one embodiment, visualization and identification can be attained by modifying a feature of at least one of the lumens relative to the other lumens. The feature may include a marking on the lumen, a diameter of the lumen or a composition of the lumen. In an additional embodiment, for brachytherapy devices in which multiple lumens are coupled to a distal end point such as a rigid connection member, visualization and identification of the lumens can be attained by modifying a feature of the rigid connection member. It will be readily appreciated that visualization and identification can be further enhanced through a combination of two or more of the techniques described herein.

3 Claims, 4 Drawing Sheets

U.S. PATENT DOCUMENTS

| | | | |
|---|---|---|---|
| 5,724,400 A | 3/1998 | Swerdloff et al. | |
| 5,741,253 A | 4/1998 | Michaelson | |
| 5,800,333 A | 9/1998 | Liprie | |
| 5,803,895 A | 9/1998 | Kronholz et al. | |
| 5,851,182 A | 12/1998 | Sahadevan | |
| 5,863,284 A | 1/1999 | Klein | |
| 6,013,020 A * | 1/2000 | Meloul et al. | 600/7 |
| 6,036,631 A | 3/2000 | McGrath et al. | |
| 6,050,930 A | 4/2000 | Teirstein | |
| 6,234,952 B1 | 5/2001 | Liprie | |
| 6,267,775 B1 | 7/2001 | Clerc et al. | |
| 6,306,074 B1 | 10/2001 | Waksman et al. | |
| 6,413,204 B1 | 7/2002 | Winkler et al. | |
| 6,416,457 B1 | 7/2002 | Urick et al. | |
| 6,458,070 B1 | 10/2002 | Waksman et al. | |
| 6,482,142 B1 | 11/2002 | Winkler et al. | |
| 6,558,390 B2 | 5/2003 | Cragg | |
| 6,607,477 B1 | 8/2003 | Longton et al. | |
| 6,616,629 B1 | 9/2003 | Verin et al. | |
| 6,685,618 B2 | 2/2004 | Tam et al. | |
| 2003/0153803 A1 | 8/2003 | Harmon | |
| 2006/0100475 A1 | 5/2006 | White et al. | |
| 2007/0167666 A1 | 7/2007 | Lubock et al. | |
| 2007/0191667 A1 | 8/2007 | Lubock et al. | |
| 2007/0270627 A1 | 11/2007 | Cutrer et al. | |
| 2008/0221384 A1 | 9/2008 | Chi Sing et al. | |

FOREIGN PATENT DOCUMENTS

| | | |
|---|---|---|
| EP | 0 867 200 | 9/1998 |
| WO | WO92/10932 | 7/1992 |
| WO | WO93/09724 | 5/1993 |
| WO | WO97/19723 | 6/1997 |
| WO | WO99/11325 | 3/1999 |
| WO | WO99/33515 | 7/1999 |
| WO | WO99/42163 | 9/1999 |
| WO | WO2008/067557 | 6/2008 |
| WO | WO2009/079170 | 6/2009 |

OTHER PUBLICATIONS

Nath, Ph.D, et al., Development of an 241 Am Applicator for Intracavitary Irradiation of Gynecologic Cancers, I.J. Radiation Oncology Biol. Phys., May 1988, vol. 14, p. 969-978.

International Search Report and Written Opinion from related PCT Application No. PCT/US2010/023454 dated May 7, 2010.

International Search Report and Written Opinion from related PCT Application No. PCT/US2010/023461 dated Jun. 1, 2010.

International Search Report and Written Opinion from related PCT Application No. PCT/US2010/033370 dated Jul. 30, 2010.

International Search Report and Written Opinion from related PCT Application No. PCT/US2010/033373 dated Aug. 9, 2010.

* cited by examiner

CATHETER MARKING FOR MULTI-LUMEN CATHETER IDENTIFICATION

FIELD OF THE INVENTION

This invention relates generally to methods and apparatus for treating proliferative tissue disorders using a multi-lumen brachytherapy device and more particularly to a system for visually distinguishing the lumens of the multi-lumen device.

BACKGROUND

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it.

Radiation therapy can be administered through one of several methods, or a combination of methods, including external-beam radiation, stereotactic radiosurgery, and permanent or temporary brachytherapy. The term "brachytherapy," as used herein, refers to radiation therapy delivered by a source of therapeutic rays inserted into the body at or near a tumor or other proliferative tissue disease site.

One interstitial brachytherapy therapy system is the Mammosite® system, provided by Hologic, Inc. of Bedford, Mass. The MammoSite system includes a catheter shaft with an inflatable balloon mounted on its distal end. A lumen extends within the catheter shaft, into the balloon. The catheter shaft is inserted into a body so that the balloon is positioned within a resected cavity. The balloon is subsequently inflated and radioactive material, for example in the form of one or more radioactive seeds, is loaded into the lumen for radiation delivery.

Mammosite® is a single lumen brachytherapy catheter. In single lumen brachytherapy catheters, the lumen is generally centered within the balloon such that the balloon generates isodose profiles in the target tissue that are substantially symmetrical, similar in shape to the inflated balloon. However, symmetric dosing may not always be desirable, as the resection cavity may not be uniform or regular in shape and size. Asymmetric dosing methods, such as those described in U.S. Pat. No. 6,749,595 include catheters with multiple lumens, where radioactive seeds may be placed within the different lumens to achieve different dosing profiles. Methods and systems for using multiple lumens for interstitial breast brachytherapy are also described by Lubbock in U.S. Patent application publication number 20070167667, Cutrer in U.S. Patent application publication number 20070142694 and Damarati in U.S. patent Ser. No. 12/369,214.

One problem with existing multi-lumen designs is that it is often difficult to visually distinguish the lumens and identify their end point locations once the device is implanted into the patient. Clearly visualizing the individual lumens in a multi-lumen brachytherapy balloon catheter is perceived as a development challenge to overcome. Radiation oncologists and physicists must be able to distinguish and identify individual lumens on a computer tomography (CT) scan that is imported into dosimetry planning software. Limitations of CT scan technology, proximity of multiple lumens to each other and limitations on the ease of manipulating scans within various dosimetry planning systems all present challenges to adequate lumen visualization and identification.

One current method for visualizing and identifying lumens includes inserting customized, dummy guidewires into the lumens to identify lumens and visualize the end of each lumen. The configurations consist of a plastic tube in which small pieces of wire are embedded at the tip and then in different staggered patterns such that a unique wire can be used in each lumen. Customization of guidewires, however, increases the overall cost of the multi-lumen device.

Commercially available standard dummy guidewires are also an option. Drawbacks of the standard guidewire design are that the length is not customized, limited unique patterns are available and materials of construction may result in too much artifact when in close proximity with other guidewires. It would be desirable to identify a method of lumen marking which overcomes the problems of the prior art.

SUMMARY

According to one aspect of the invention a system and method for enhancing the ability to visualize and identify lumens in a multi-lumen device involves modifying a feature of at least one lumen and/or modifying a feature of a member which couples the lumens.

In one embodiment, the features of the lumens which may be modified to distinguish the lumens includes, but is not limited to, a marking on the lumen, a diameter of the lumen and a composition of the lumen. For example, a multi-lumen brachytherapy device may comprise markings located on or about the multiple lumens to assist in the visualization and identification of the individual lumens during CT scans. In one embodiment at least one lumen in a multi-lumen brachytherapy device is printed with a unique pattern using radio-opaque ink. For example, the exterior surface of the printed lumen may be marked at its distal tip and then in a unique pattern down at least a portion of its length. With such an arrangement visualization of the tip of the lumen is achieved with reduced artifact. The 'built in' nature of the markings enables visualization without the addition of specialized accessories, reducing the overall transfer cost of the brachytherapy device. As will be described later herein, in alternative embodiments two or more of the lumens may be formed from material having a different radiographic contrast to distinguish the lumens during imaging or two or more lumens may have different diameters.

According to another aspect of the invention, a distal tip of the multi-lumen brachytherapy device comprises a connection member which couples the distal tips of the multiple lumens. In one embodiment certain features of the connection member may be altered to facilitate identification of the lumens, where the features that may be altered include but are not limited to the connection points between the lumens and the member, the body of the member and the composition of the member. For example, the distal tip may be formed to include one or more different marking at the different connection points of the individual lumens to allow differentiation of the lumens in a transverse (axial) CT scan image. Alternatively, a perimeter of the connection member may be marked at points related to lumen position to facilitate lumen identification. In still another embodiment the distal tips of the lumens may be distinguished by forming the connection member from a material having a different radiographic contrast than that of the lumens.

DETAILED DESCRIPTION

Systems and methods that facilitate visualization and identification of lumens of a multi-lumen brachytherapy device are disclosed. In one embodiment, visualization and identification can be attained by modifying a feature of at least one of the lumens relative to the other lumens. The feature may include a marking on the lumen, a diameter of the lumen or a composition of the lumen. In an additional embodiment, for brachytherapy devices in which multiple lumens are coupled to a distal end point such as a rigid connection member, visualization and identification of the lumens can be attained by modifying a feature of the rigid connection member. It will be readily appreciated that visualization and identification can be further enhanced through a combination of two or more of the techniques described herein.

Figure 1:
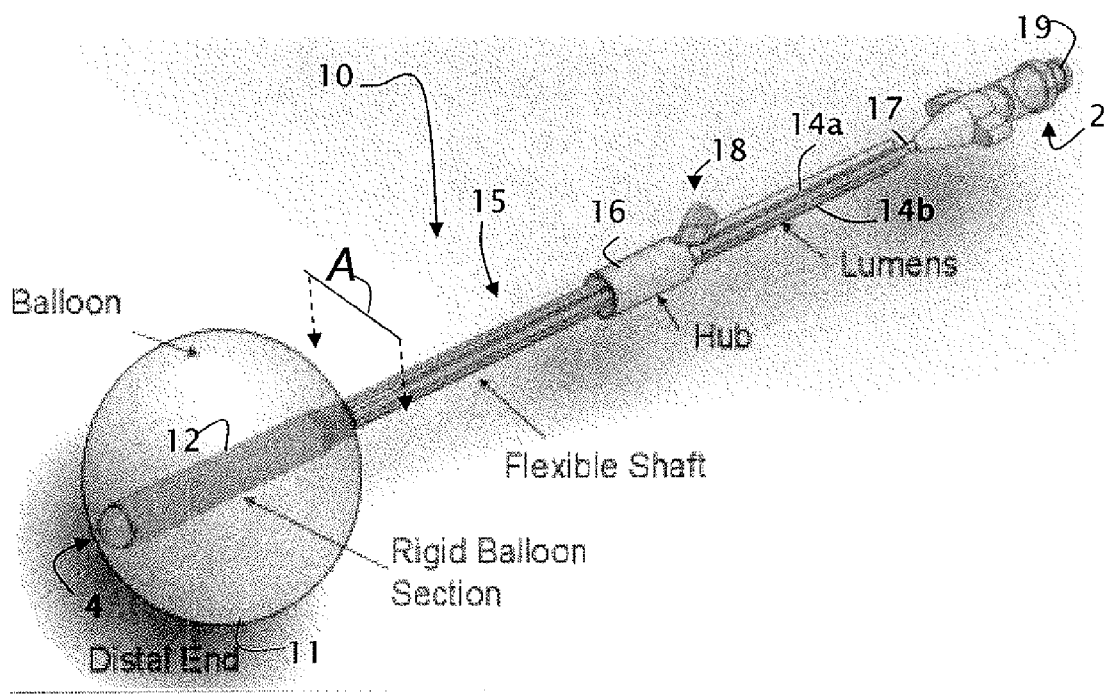
FIG. 1 illustrates a multi-lumen brachytherapy device which may be adapted using one or more of the principles of the present invention to facilitate visualization and identification of the lumens.

FIG. 1 illustrates an example of a multi-lumen brachytherapy catheter which may use one or more of the techniques of the present invention to distinguish lumens. A brachytherapy device 10 includes a flexible shaft 15 including a proximal end 2 and a distal end 4. The flexible shaft is comprised of a plurality of flexible dosing lumens 14a and 14b and an inflation lumen 17. Each dosing lumen is sized to accommodate one or more radiation sources for customization of radio-isotope treatment profiles. It should be noted that although only two dosing lumens are visible in FIG. 1, the present invention may be implemented with any number of dosing lumens. The inflation lumen 17 is coupled at a proximal end to a connector 19. The lumens 14a, 14b and 17 are made, for example, from flexible or semi-flexible types of extruded tubing. Each lumen 14a, 14b, 17 slideably extends through holes in the hub 16 and into openings which extend longitudinally into the rigid connection member 12. In one embodiment the openings in the rigid connection member are sized so that the exterior of each lumen is tightly received in its respective opening. The lumens may be fixedly attached to the rigid connection member 12 using an adhesive.

An inflatable member, shown as balloon 11, envelops at least a portion of the rigid connection member 12. In operation, the inflatable member is inflated by coupling the device to a source of a gas or other liquid via connector 19. The inflation liquid flows into the member via the inflation lumen 17. One or more inflation holes (not shown) extend through the inflation lumen and rigid connection member into the inflatable member. When the inflatable member is positioned in the resected cavity, the gas or other liquid is forwarded through the inflation lumen into the inflatable member to secure the member within the cavity. Once the member is inflated, connector 19 is detached from the source.

The hub 16 collects but does not connect the lumens; in some embodiments, the portion of the flexible shaft between a distal end of the hub and a proximal end of the rigid balloon section may be sheathed in a catheter, although it is not a requirement of the invention. The hub 16 includes one or more holes extending there through, where the holes in the hub have clearance tolerances that allow the lumens to independently move axially and rotatably within the hub.

Because the multiple lumens of the device 10 are flexible and independently moveable both axially and rotationally, forces experienced at the proximal end of the device 10 do not translate into movement at the distal end of the device. Reducing the propensity for movement of the shaft also increases the comfort of the patient.

Clear visualization and identification of the lumens is important to dosimetry planning and implementation but is difficult due to the close spacing of the lumens. As described above the present invention facilitates the visualization and identification through modification of one or more features of the lumens or connection member as will be described with reference to FIGS. 2-7.

Figure 2:
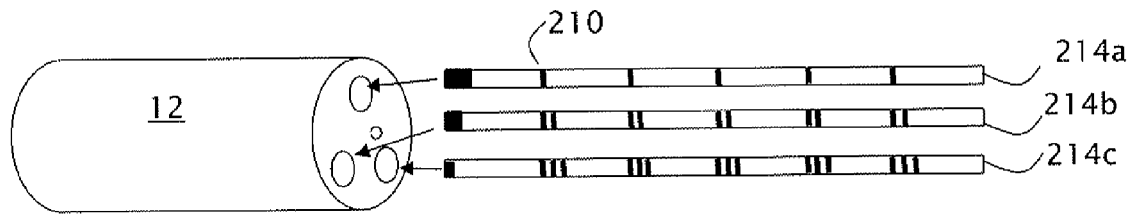
FIG. 2 illustrates a plurality of lumens of the present invention which are printed in various patterns to increase visualization and identification.
Figure 3:
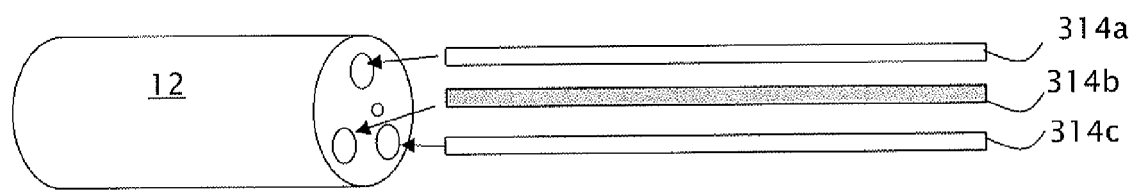
FIG. 3 illustrates a plurality of lumens of the present invention which are formed from material having different radiographic contrast.
Figure 4:
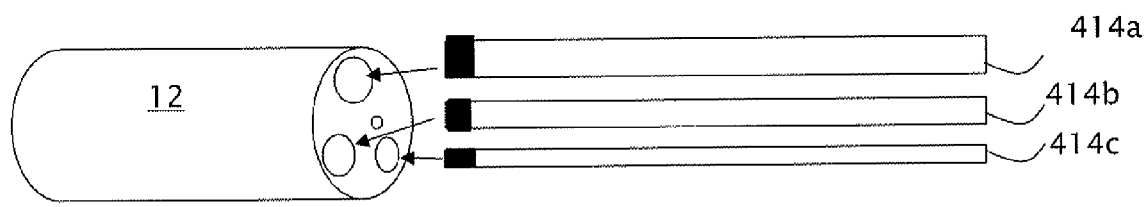
FIG. 4 illustrates another embodiment whereby the feature of each lumen that differs is their diameter.

FIGS. 2-4 illustrate how features of the lumens may be modified to visually differentiate them for identification purposes. As shown in FIG. 2, each of the dosing lumens 14a, 14b and 14c are uniquely marked with radio-opaque ink, for example each having a different pattern of radio-opaque markings 210. For example Radio-opaque™ Ink developed by CI Medical Inc., of Norton Mass. or other equivalent may be used. In one embodiment, the exterior surface of each lumen is printed at the tip and along its length with its individual pattern prior to coupling to the rigid member. As a result visualization of the tip and differentiation of the lumens may be achieved without additional guide wires or accessories. In one embodiment the markings may be made at predefined increments (cm, mm) to provide reference measurement points to users for placement and observation of radioactive material. One advantage of using radio-opaque ink, as opposed to wrapping the lumen with wire or other radio-opaque material is that the device is lighter and there is no chance that the markers may change positions.

In an alternative embodiment illustrated in FIG. 3 the lumens 314a, 314b, 314c may be made of material having different radiographic contrast (measured in terms of Hounsfield units) to maximize contrast and clarity between the lumens and reduce material artifact.

FIG. 4 illustrates another embodiment whereby the feature of each lumen that differs is their diameter. The use of a lumen with a different diameter and comprised of a material sufficient to be provide imageable contrast, may be used in conjunction with a marker at the tip of the lumen to visualize the lumen tip as well as differentiate the lumens, as the relative diameters will be readily ascertainable in the resulting image.

Figure 5A:
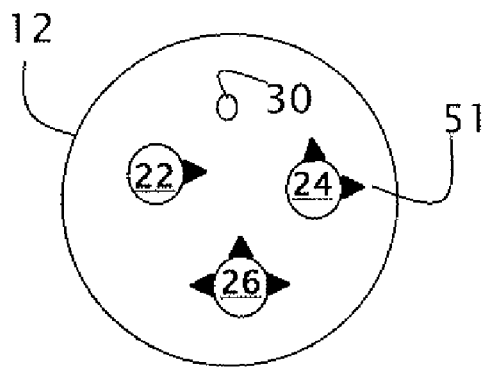
FIGS. 5A-5C illustrate a variety of embodiments for marking a rigid portion of the brachytherapy device of FIG. 1 to assist in the visualization and identification of the lumens.
Figure 5B:
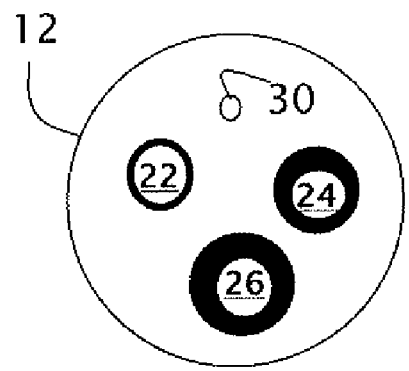
Figure 5C:
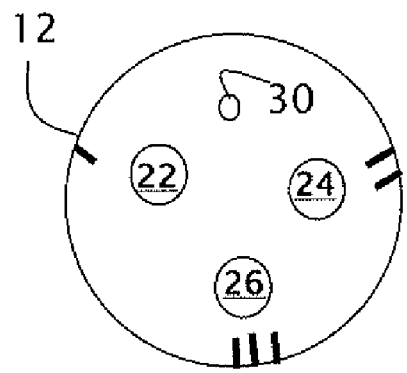

FIGS. 5A-5C are cross-section images of the rigid member, taken along plane A of FIG. 1. It is known that different elements have different radiographic contrast (measured in Hounsfield units) which provides a resultant image that is either lighter or darker. As a reference, water is 0H, Air is −1000 H (appears darker) and Titanium is +1000 H (appears lighter). According to one aspect of the invention it is realized that the rigid member may be formed with features that capture air. The features may surround the openings into which the lumens are extended so that cross-sectional views, identifiable via a transverse CT scan, will display the features and facilitate identification of the individual lumens. Alternatively the features may be cut into the rigid connection member, either on the periphery, or as through holes, etc., in positions that are proximate to the lumens.

FIGS. 5A and 5B illustrate embodiments wherein the features are positioned near the openings of the member which connect to the lumens. In one embodiment the connection member is formed a photosensitive resin using stereolithography to define the dosing lumen openings 22, 24 and 26 and inflation lumen opening 30. Alternatively the connection member could be machined, or the part may be formed using an extrusion process. The openings in FIG. 5A are sized in accordance with the diameter of the lumens to form a tight fit between the lumens and the connection device. In addition notches 51 may be drilled at the edges of the openings. Each opening may have a different number of notches ranging from 0 to N, where N is the number of openings. The air pocket that is naturally within each notch provides a dark marking on the scan image, allowing individual lumens to be identified with ease.

FIG. 5B illustrates a different embodiment where the lumen opening size is varied for lumen identification. For example, lumen opening 22 is smallest, lumen opening 24 is medium and lumen opening 26 is largest. In such an embodiment, the lumen is coupled to the rigid member using an adhesive at its tip, and an air pocket is therefore formed around the lumen within the rigid member. As shown in FIG. 5B the air pockets that result from the different size openings allow the individual lumens to be distinguished.

FIG. 5C illustrates an embodiment wherein the peripheral body of the connection member is scored with notches. The location of scoring relates to the location of the lumen holes; it need not directly relate as long as the relation is known to the observer. As shown in FIG. 5C scoring is different for each lumen location.

Other methods of notching, scoring or modifying the connection member to generate air pockets that can be visualized to distinguish the lumens include drilling holes of varying sizes proximate to each lumen hole, scoring different shapes at the peripheries (box, arc, x, etc.) and the like.

Figure 6:
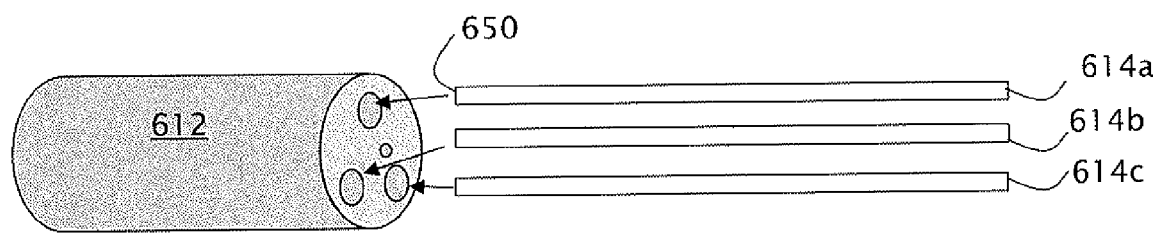
FIGS. 6 and 7 illustrate the rigid portion of the catheter and the lumens having differing radiographic contrast.
Figure 7:
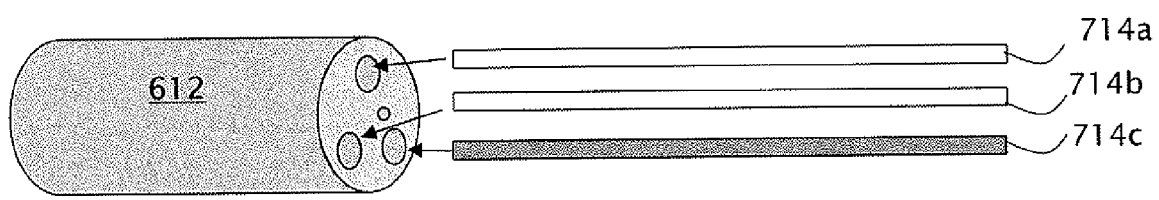

FIGS. 6 and 7 illustrate embodiments of the invention where the composition of the lumen and connection member is selected to facilitate location of the distal tip 550 of the lumen. In FIGS. 6 and 7 the shading of the element is related to the radiographic contrast of the element; in FIG. 6 the lumens are of a higher contrast than the connecting member and the intersection of the two different types of materials allows the endpoint of the lumen to be identified with increased precision. In FIG. 7, in addition to the connection member, each of the lumens is made from a material having a different contrast, helping to distinguish the lumens from each other as well as enhancing end point identification.

According a method of making a multi-lumen catheter device may include adding features to either of the lumens or a member connecting the lumens to enhance lumen visualization and identification. The methods include printing the lumens distinct patterns using radio-opaque ink and/or manufacturing the lumens using materials of differing radiographic contrast. The methods also include adding a feature to the connection member during its formation, where the feature includes one of notches, holes or other removal of material of the connection member near or about lumen connection points to form air gaps in the connection member, such air gaps being used for identification of the lumens and visualization of lumen end point locations.

Having described several preferred embodiments of the invention it should be appreciated that there are many ways in which the concepts of the present invention may be combined to provide a multi-catheter device with improved visibility. All of the combinations are within the scope of the present invention. In addition although certain materials are disclosed it should be noted that the materials are provided merely by way of example and the present invention may be practiced with a variety of equivalent substitute materials. In addition, although the invention has been described with regard to a breast brachytherapy device it is appreciated that the concepts may be extended for use in any device that requires precise imaging information.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

The invention claimed is:

1. A multi-lumen brachytherapy device for treating breast cancer comprising:
   a plurality of lumens, wherein each of the plurality of lumens comprises a feature having a radio-opaque printed marking with a unique pattern which differentiates it from the other lumens and that facilitates visualization and identification of the lumens during breast cancer treatment.

2. A multi-lumen treatment device comprising:
   a plurality of lumens, each having a proximal end and a distal end wherein each of the lumens is fabricated from a material that differs in radiographic contrast from at least one other lumen to facilitate visualization and identification of the lumen during treatment.

3. The multi-lumen treatment device of claim 2 wherein the at least one lumen is a radiation dosing lumen.

* * * * *